US00PP27464P3

(12) United States Plant Patent
Layt

(10) Patent No.: US PP27,464 P3
(45) Date of Patent: Dec. 13, 2016

(54) ***FESTUCA ARUNDINACEA* PLANT NAMED KT12**

(50) Latin Name: *Festuca arundinacea*
Varietal Denomination: KT12

(71) Applicant: Todd Anthony Layt, Richmond (AU)

(72) Inventor: Todd Anthony Layt, Richmond (AU)

( * ) Notice: Subject to any disclaimer, the term of this patent is extended or adjusted under 35 U.S.C. 154(b) by 0 days.

(21) Appl. No.: 14/545,550

(22) Filed: May 20, 2015

(65) Prior Publication Data

US 2015/0351304 P1 Dec. 3, 2015

Related U.S. Application Data

(60) Provisional application No. 62/003,082, filed on May 27, 2014.

(51) Int. Cl.
*A01H 5/12* (2006.01)

(52) U.S. Cl.
USPC ..... Plt./388

(58) Field of Classification Search
USPC ..... Plt./388
See application file for complete search history.

*Primary Examiner* — Annette Para
(74) *Attorney, Agent, or Firm* — Samuel R. McCoy, Jr.

(57) ABSTRACT

A new and distinct turf grass cultivar of *Festuca arundinacea* plant named 'KT12', characterized by the combination of a large number of rhizomes, long rhizomes, and a dense growth habit; characteristics which translate to a highly aesthetic turf grass that exhibits improved environmental tolerances and lower production and maintenance input costs.

2 Drawing Sheets

Latin name of genus and species of plant claimed: The Latin name of the genus and species of the novel variety disclosed herein is *Festuca arundinacea.*

Variety denomination: The novel variety of *Festuca arundinacea* disclosed herein has been given the variety denomination 'KT12'.

REFERENCES CITED

U.S. Patent Documents

U.S. Pat. No. 6,677,507, January 2002, de Bruijn

BACKGROUND OF THE INVENTION

The present invention relates to a new and distinct perennial variety of *Festuca arundinacea*, commonly identified as tall fescue grass, which has been given the variety denomination of 'KT12'. Its market class is PLT/388 and is commonly classified by the ornamental horticulture industry as a cool season turf grass. When seed is sown at a relatively high density, tall fescue creates a dense turf with a medium to coarse texture which is suited to climates from the northern United States and extending south to the "Transition Zone".

Cool season turf grasses, such as tall fescue, typically exhibit a clumping or "tillering" growth habit whereby multiple stems arise from a single seedling but do not spread laterally. By contrast, warm season turf grass species exhibit a spreading habit, which is made possible by above-ground prostrate stems known as stolons and also by below-ground lateral running root structures known as rhizomes. There are a myriad of benefits of turf grasses which possess stolons and rhizomes including but not limited to: improved drought tolerance, improved heat and cold tolerance, improved wear tolerance, faster recovery from injury, and improved aesthetics. These attributes also contribute to reduced production costs for turf grass producers and reduced maintenance costs for end users. Consequently, it has long been the objective of tall fescue breeding programs to develop varieties that possess either or both stolons and rhizomes in order to develop a superior turf grass variety.

Parentage: The new *Festuca arundinacea* cultivar is a seedling selection of *Festuca arundinacea* 'Torpedo' (unpatented) resulting from a multi-generational, open-pollination breeding program conducted from 2004 to 2011 at a commercial plant breeding facility in Richmond, NSW, Australia with the primary objective of developing a highly rhizomatous tall fescue variety. To initiate the breeding program, seeds from 'Torpedo' were germinated in 2004 and again in 2005. These two crops resulted in approximately one thousand rooted seedlings, from which two hundred progeny were identified as possessing a greater number of rhizomes and a denser growth habit when compared with the seed parent and other sibling seedlings. These two hundred plants were subsequently potted into 140 mm nursery pots for further observation. After further observation, those plants that were identified as the most rhizomatous of these plants were potted into 200 mm nursery pots for further observation and were allowed to cross-pollinate. Seed was subsequently harvested from those plants that exhibited the greatest number of rhizomes. These seeds were later germinated in 162-cell propagation plug trays, resulting in approximately 648 rooted plugs. In autumn 2006 (approximately April in the Southern Hemisphere), approximately one hundred plants with the greatest number of rhizomes were isolated and potted into 140 mm nursery pots for further observation. In early Spring 2006 (which approximates to September in the Southern Hemisphere), twenty plants which were observed to be the most rhizomatous plants, and also observed to exhibit a slightly denser growth habit, were selected and potted into 200 mm nursery pots. Said twenty plants were allowed to grow adjacent to forty-eight 140 mm nursery pots containing common *Festuca*

*arundinacea* plants, which are non-rhizomatous. The breeding progeny were allowed to openly cross-pollinate with the common *Festuca arundinacea* plants. The breeding progeny were also manually cross pollinated by the breeder. In approximately December 2006, seed was harvested from the twenty progeny plants and germinated in propagation plug trays, resulting in one hundred and twenty-three seedlings. In approximately April 2007, the breeder isolated fifty plants that exhibited a combination of the greatest number of rhizomes and the longest rhizomes, and also ten plants that exhibited the densest growth habit from the one hundred and twenty-three seedlings harvested in December of 2006. These sixty plants were potted into 140 mm nursery pots. Said plants were allowed to openly cross-pollinate and were also manually pollinated by the breeder. From these sixty plants, ten plants were observed to be highly rhizomatous and exhibit a relatively dense growth habit. Seeds were harvested from each of these ten plants and later germinated in propagation plug trays which resulted in one hundred and twenty-eight seedlings. These seedlings were subsequently potted into 90 mm nursery pots and labelled "KT1" to "KT128", corresponding to each of the one hundred and twenty-eight plants. In approximately October of 2008, twenty plants which were observed to be highly rhizomatous and exhibited a relatively dense growth habit were potted on into 200 mm nursery pots for further observation. In approximately April of 2008, each of the twenty plants were removed from the nursery pot and the number and length of rhizomes were recorded. One of said plants, identified as 'KT12', was observed to exhibit significantly more rhizomes and longer rhizomes. Some of the other accessions from the breeding program were also observed to exhibit a relatively high number of rhizomes, but 'KT12' had longer rhizomes than all other accessions and also exhibited a larger number of rhizomes growing from the bottom of the pot. Based on these observations, 'KT12' was isolated for further trials and evaluation.

Asexual Reproduction: 'KT12' was first asexually propagated by division of rhizomes in 2008 in Richmond, NSW, Australia. 'KT12' has since been further asexually propagated by means of cutting and division of rhizomes. The distinctive characteristics of the variety have remained stable and true to type through successive cycles of asexual propagation.

SUMMARY OF THE INVENTION

A new and distinct turf grass cultivar of *Festuca arundinacea* plant named 'KT12', characterized by the combination of a large number of rhizomes, long rhizomes, and a dense growth habit; characteristics which translate to a highly aesthetic turf grass that exhibits improved environmental tolerances and lower production and maintenance input costs.

BRIEF DESCRIPTION OF THE PHOTOGRAPHS

DETAILED BOTANICAL DESCRIPTION

Figure 1:
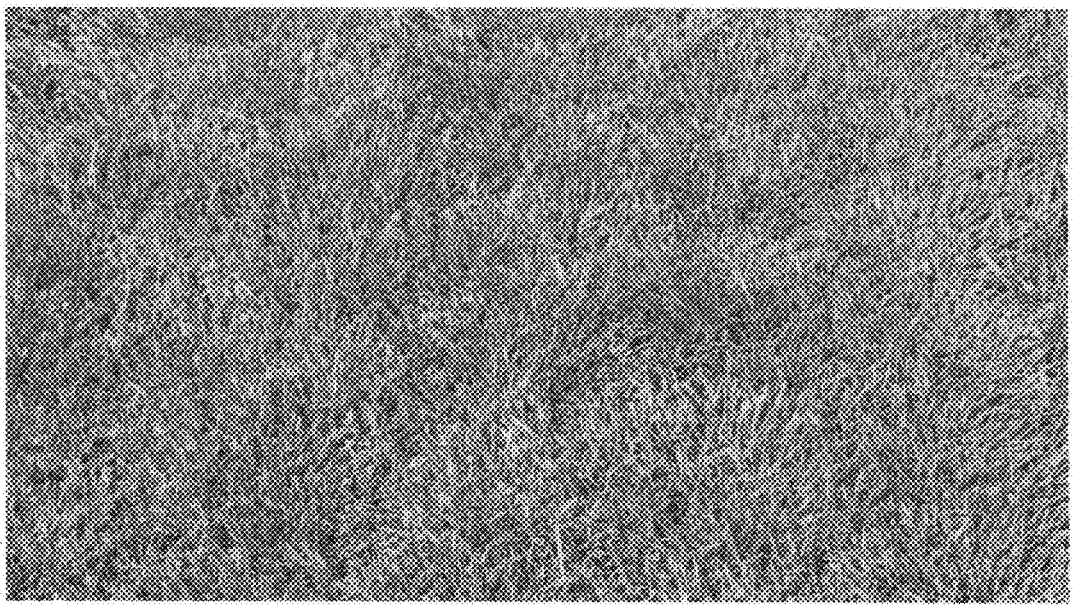
FIG. 1 illustrates, as nearly true as it is reasonably possible to make the same in color illustrations of this type, typical foliage and growth characteristics of the new cultivar. Colors in the photographs differ slightly from the color values cited in the detailed description, which accurately describes the colors of 'KT12'.
Figure 2:
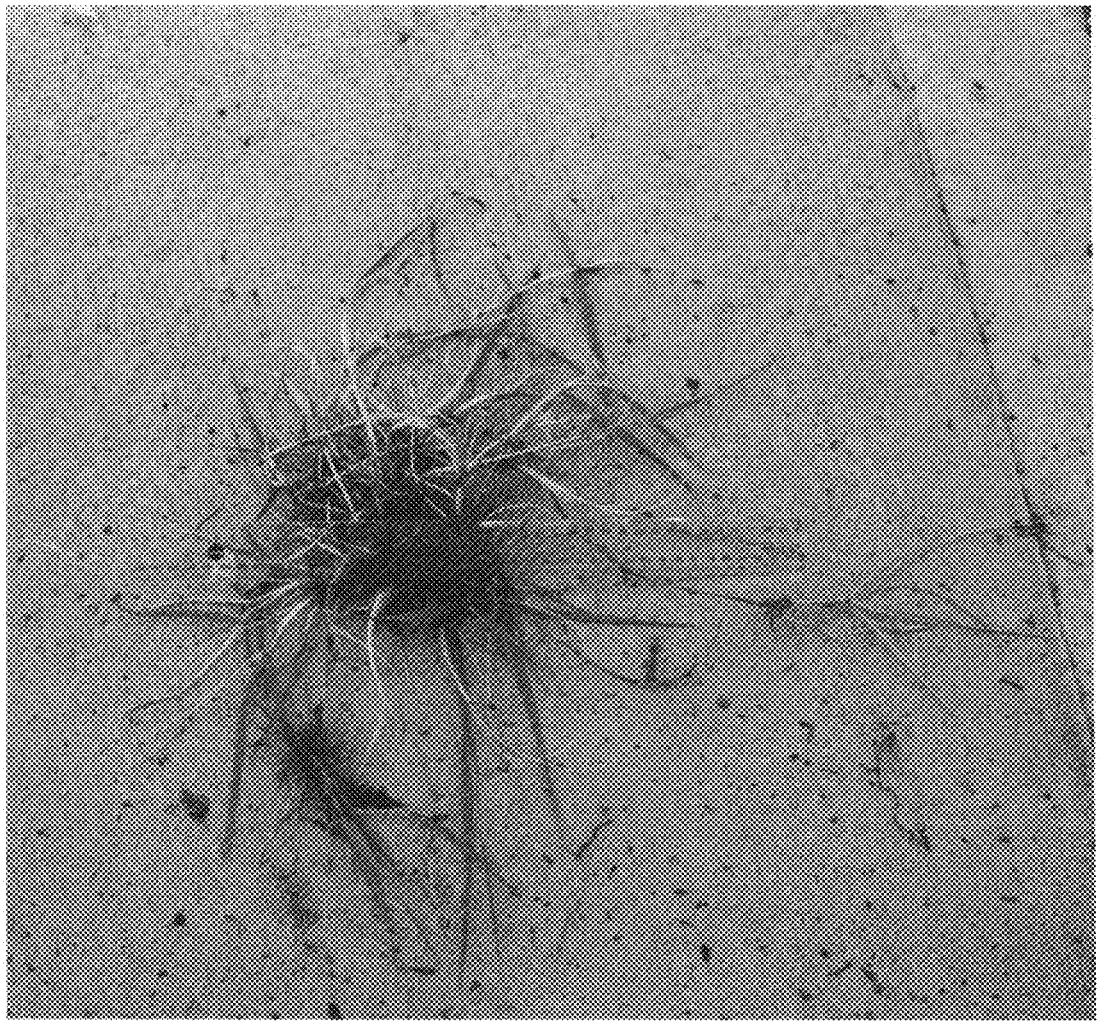
FIG. 2 illustrates the exemplary high number and long length of rhizomes of 'KT12', shown with a 40 cm ruler for scale.

The following is a detailed botanical description of a new and distinct variety of a *Festuca arundinacea* turf grass plant known as 'KT12'. Plant observations were made on plants grown in Awendaw, S.C., USA. Unless indicated otherwise, the descriptions disclosed herein are based upon observations made in May 2014 of mature and unpruned 'KT12' plants, approximately 15 months old, grown in 3 gallon nursery pots filled with soilless potting media, maintained with granular slow release fertilizer in an outdoor growing area and regularly watered with overhead irrigation. No pest and disease measures were taken.

Those skilled in the art will appreciate that certain characteristics will vary with older or, conversely, younger plants. 'KT12' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Color Chart, of The Royal Horticultural Society, London, 1986 edition.

TECHNICAL DESCRIPTION OF THE VARIETY

Plant description:

*Growth habit*.—A long-lived, spreading perennial grass with an upright to decumbent growth habit forming a dense mat foliage on the ground surface.

*Height*.—Measured from soil level, the sward of 'KT12' exhibits a general approximate height of 20 cm with the tallest blades reaching 28 cm above soil level, as measured. It should be noted that, based on the morphology of the species, it is believed that 'KT12' will likely reach a height of approximately 100 cm when planted in the ground and under optimal conditions.

*Width*.—60 cm, as measured.

*Growth rate*.—Moderate to vigorous.

*Bloom period*.—Spring.

*Hardiness*.—USDA Zone 2 to 8.

*Environmental tolerances*.—Prefers to be grown in full sun but will tolerate partial shade. Relatively drought and heat tolerant once established; better than the species and other cultivars known to the breeder. Tolerates a wide range of soil types from sandy loam to loamy clay.

*Pest and disease susceptibility or resistance*.—In common with the species, none of note.

*Propagation*.—Propagation is accomplished through division of rhizomes. Typical time to develop roots is approximately 2 to 4 weeks and an average crop time to produce an initial mature and marketable stand of turf grass sod is approximately 8 to 12 months. Precise timing varies depending on planting method, planting density, fertilizer and water inputs as well as geographical location.

Roots:

*General description*.—Root system consists of numerous coarse and fibrous feeder roots as well as a network of rhizomes of various lengths, ranging from short to relatively long.

*Number of rhizomes*.—Numerous.

*Length of rhizomes*.—Ranging from 5 to 60 cm.

*Rhizome internodes*.—Length ranges from 4 to 6 cm.

Foliage:

*Attachment*.—Cauline.

*Length of blade*.—Mature blades are an average of 18 cm.

*Width of blade*.—6 mm at widest point.

*Shape of blade*.—Linear.

*Leaf shape; apex*.—Acute.

*Leaf aspect*.—Concave.

*Margin*.—Serrulate.

*Texture of top surface*.—Glabrous.

*Texture of bottom surface*.—Glabrous.

*Leaf color* (*adaxial & abaxial surface*).—Juvenile: Green (RHS 137A); mature: Yellow-green (RHS 147A).

*Venation*.—Type — Parallel.

*Venation color*.—Indistinguishable.

*Leaf sheath*.—Split with margins overlapping and approximately 10 to 15 mm long; glabrous. Color approximates to Green 137A.

*Collar*.—Broad; extending from leaf margin to leaf margin. Length is approximately 3 mm long, from the sheath to the leaf blade. Color approximates to Yellow-Green 145B.

*Ligule*.—Membranous; approximately 1.5 mm long; pubescent. Color appearing to be similar to the culm, Green (RHS 137C).

*Auricle*.—Rudimentary; short and rounded.

*Culm attitude*.—Upright to semi-decumbent.

*Culm length*.—Longest measuring 48 mm from base of shoot to panicle base.

*Culm internode length*.—Ranging from 10 to 20 mm.

*Culm color*.—Green (RHS 137C).

*Flag leaf dimension*.—Most mature flag leaf measuring 48 mm long and 9 mm wide.

*Flag leaf color* (*adaxial & abaxial surface*).—Juvenile: Green (RHS 137A); mature: Yellow-green (RHS 147A).

Inflorescence:

*Natural flowering season*.—Spring in Northern hemisphere, April to June.

*Inflorescence type and habit*.—Panicle.

*Total inflorescence size, including peduncle*.—230 mm long by 2.5 mm wide.

*Quantity of inflorescences*.—Numerous; greater than 40.

*Quantity of florets per panicle*.—Approximately 60 to 80.

*Pedicel*.—8 to 10 mm long and thin, less than 1 mm wide; color is Green (RHS 137B).

*Rachilla*.—Slightly curved; approximately 1.5 mm long and less than 1 mm wide; color is Green (RHS 137B).

Floret:

*Dimensions of florets*.—Approximately 8 mm long and 2.5 mm wide.

*Color of florets*.—A combination of Yellow-Green (RHS 144A) and Yellow-Green (RHS 144B).

*Glumes*.—Two: first approximately 4.5 mm long and the second is approximately 5.5; color of both glumes is Yellow-Green (RHS 144B).

*Lemma & palea*.—Both approximately 9 to 10 mm long, including awns; color is Yellow-Green (RHS 144B); Length of awns is 4 mm.

Reproductive organs: Not observed.

Seeds and fruits: Not observed.

COMPARISON OF 'KT12' WITH OTHER VARIETIES OF *FESTUCA ARUNDINACEA*

The closest known varieties to 'KT12' are the seed parent, 'Torpedo' and *Festuca arundinacea* 'Bar Fa 08PB'. All three varieties have similar plant dimensions, growth habits and leaf characteristics and all are noted as being significantly more rhizomatous when compared to the species and other *Festuca arundinacea* turf grass cultivars. However, 'KT12' is observed to exhibit more rhizomes and longer rhizomes than both the seed parent and 'Bar Fa 08PB'. 'KT12' is observed to possess 18 rhizomes of varying lengths in a 15 month-old 3 gallon nursery pot whereas 18 month-old plants of 'Torpedo' exhibit a range of 0 to 12 rhizomes and 'Bar Fa 08PB' exhibit a range of 0 to 10 rhizomes when grown in the ground. Both 'Torpedo' and 'Bar Fa 08PB' do not exhibit a rhizomatous habit in all plants whereas all 'KT12' plants in a population will have rhizomes. 'KT12' has rhizomes of varying length with the longest rhizomes reaching 60 cm long whereas the longest rhizomes of 'Torpedo' reach 48 cm and the longest rhizomes of 'Bar Fa 08PB' reach 33 cm.

That which is claimed is:

1. A new and distinct variety of *Festuca arundinacea* plant named 'KT12', substantially as described and illustrated herein.

* * * * *